United States Patent
Kimchy et al.

(10) Patent No.: US 8,401,611 B2
(45) Date of Patent: Mar. 19, 2013

(54) APPARATUS AND METHOD FOR IMAGING TISSUE

(75) Inventors: Yoav Kimchy, Haifa (IL); Gideon Baum, Haifa (IL)

(73) Assignee: Check-Cap Ltd., Isfiya (IL)

( * ) Notice: Subject to any disclaimer, the term of this patent is extended or adjusted under 35 U.S.C. 154(b) by 54 days.

(21) Appl. No.: 12/996,386

(22) PCT Filed: Jun. 4, 2008

(86) PCT No.: PCT/IL2008/000765
§ 371 (c)(1),
(2), (4) Date: Dec. 5, 2010

(87) PCT Pub. No.: WO2008/149362
PCT Pub. Date: Dec. 11, 2008

(65) Prior Publication Data
US 2011/0077505 A1    Mar. 31, 2011

(51) Int. Cl.
*A61B 5/05* (2006.01)
(52) U.S. Cl. .................................................. 600/407
(58) Field of Classification Search ............... None
See application file for complete search history.

(56) References Cited

U.S. PATENT DOCUMENTS

| 5,643,297 | A | 7/1997 | Nordgren et al. |
| 5,677,539 | A | 10/1997 | Apotovsky et al. |
| 6,389,183 | B1 | 5/2002 | Han |
| 2001/0010013 | A1 | 7/2001 | Cox et al. |
| 2004/0092807 | A1 | 5/2004 | Breskin et al. |
| 2005/0215990 | A1 | 9/2005 | Govari |
| 2006/0041199 | A1 | 2/2006 | Elmaleh et al. |
| 2006/0188065 | A1 | 8/2006 | Razzano et al. |
| 2006/0195032 | A1 | 8/2006 | Iwanczyk et al. |
| 2007/0161885 | A1 | 7/2007 | Kimchy |

OTHER PUBLICATIONS

Optical Technique Identifies Vulnerable Plaques in Cardiac Patients; May 28, 2005; Massachusetts General Hospital.
Frank, H. (2001). Characterization of atherosclerotic plaque by magnetic resonance imaging, in American Heart Journal, Feb. 2001, pp. S45-S48.
Shi, Y. et al. (2005). Identification of vulnerable atherosclerotic plaque using IVUS-based thermal strain imaging. IEEE Transactions on Ultra-sonics, Ferroelectrics, and Frequency Control, vol. 52, No. 5, May 2005, pp. 844-850.
Casis, L.A. et al. (1998). Cardiovascular Near-Infrared Imaging. Nir Publication, 6, A21-A25.
Molecular Imaging Allows Detection of Plaques Likely to Rupture; Dietary Modification, Statins May Stabilize Vulnerable Plaques, Dec. 20, 2005. SNM—Advancing Molecular Imaging and Therapy.

*Primary Examiner* — Brian Casler
*Assistant Examiner* — Saurel J Selkin
(74) *Attorney, Agent, or Firm* — Soroker Agmon

(57) ABSTRACT

A device and method for imaging body tissue, the device comprising a catheter for accessing body cavities having a catheter end, the catheter end having there within an ionizing radiation source for emitting ionizing radiation; and at least one ionizing radiation detector for detecting ionizing radiation; and wherein preferably a signal is emitted by the ionizing radiation source, said signal comprising photons or electrons, said photons or electrons are reflected from the body tissue or provoke the body tissue to generate photons or electrons.

17 Claims, 7 Drawing Sheets

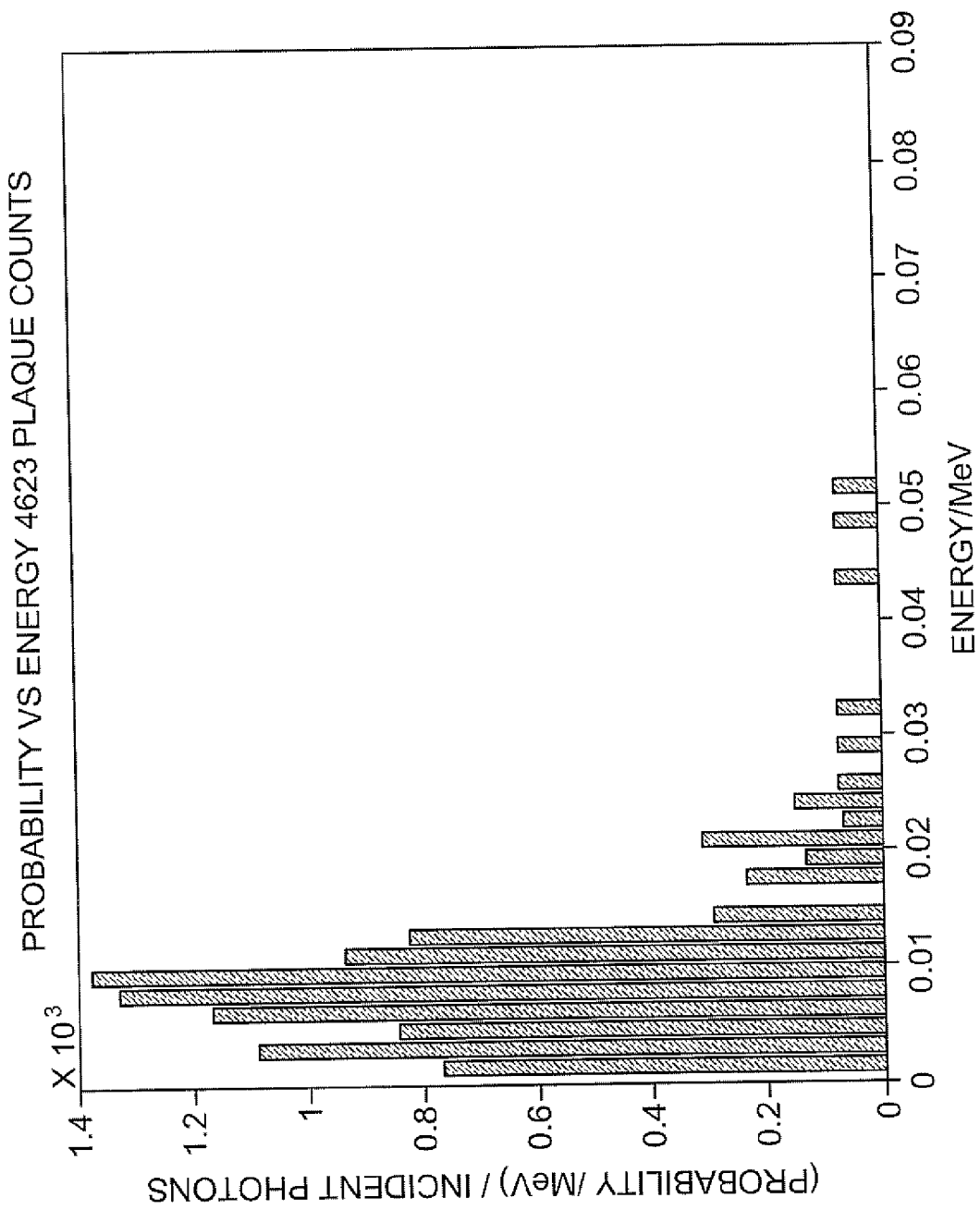

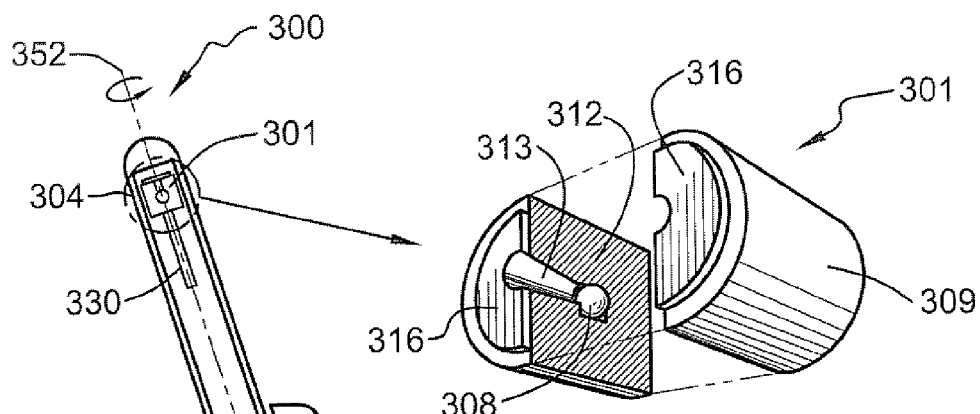
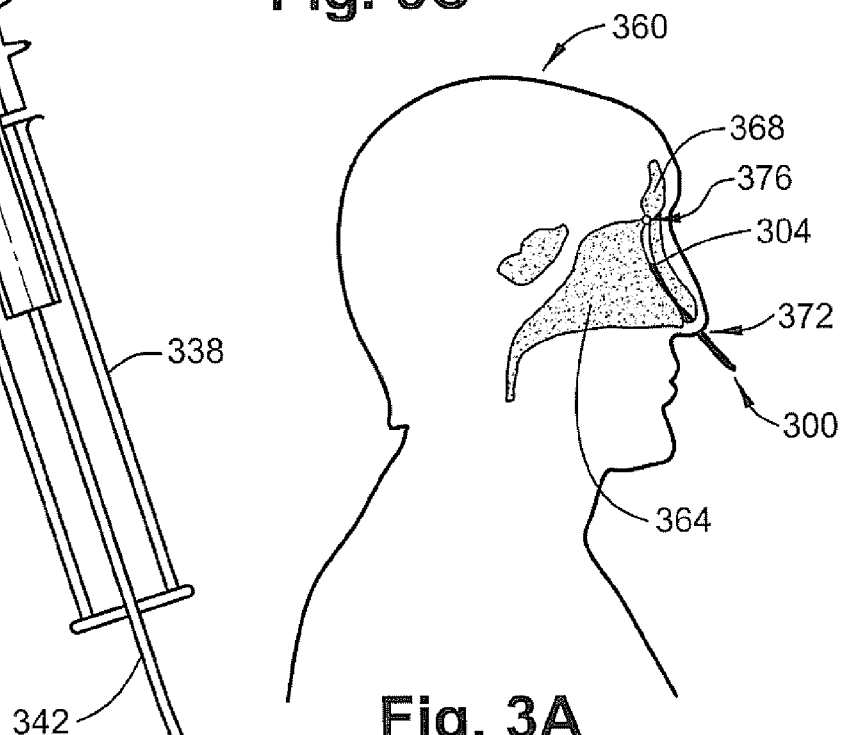
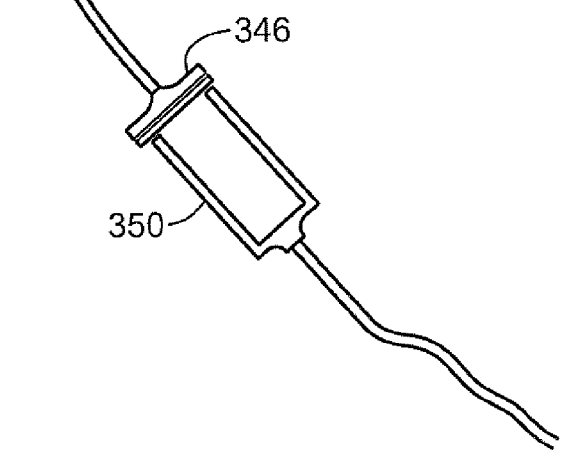
Fig. 3C
Fig. 3A
Fig. 3B

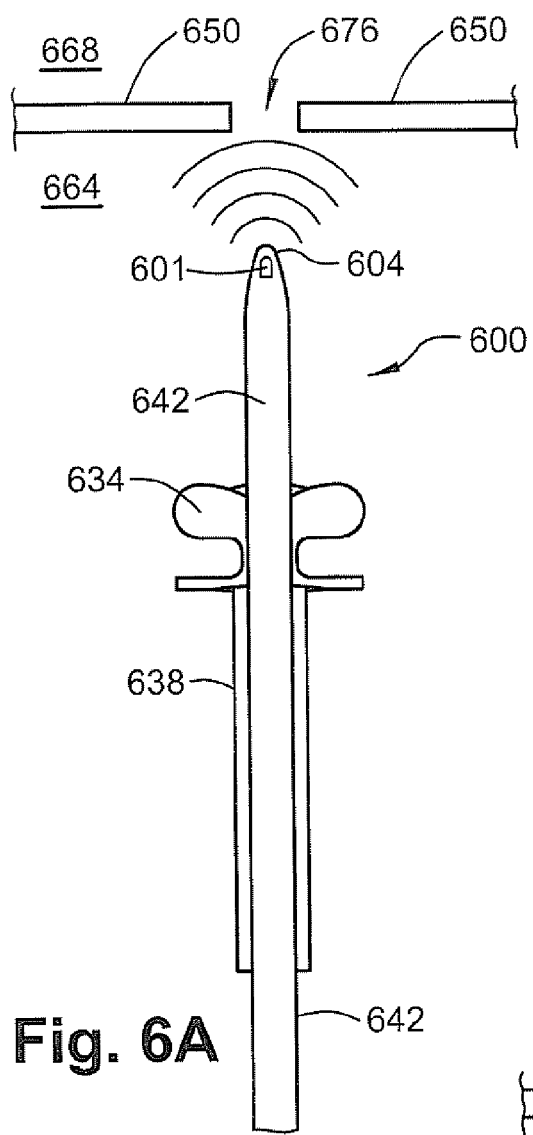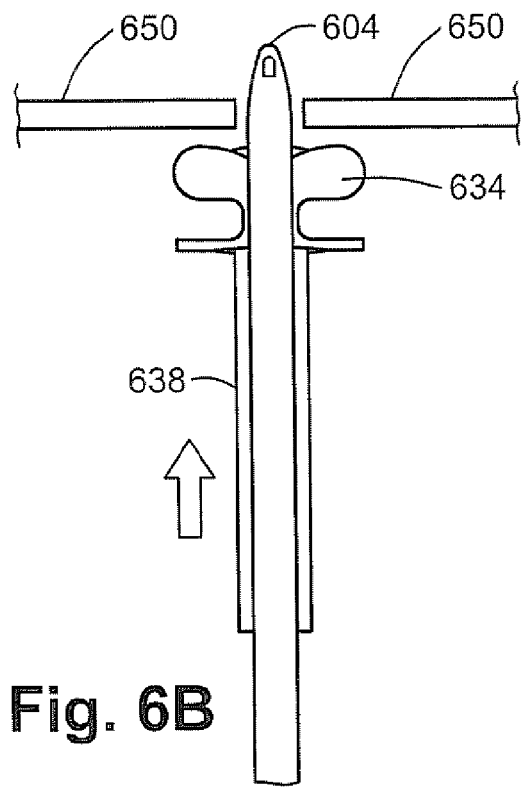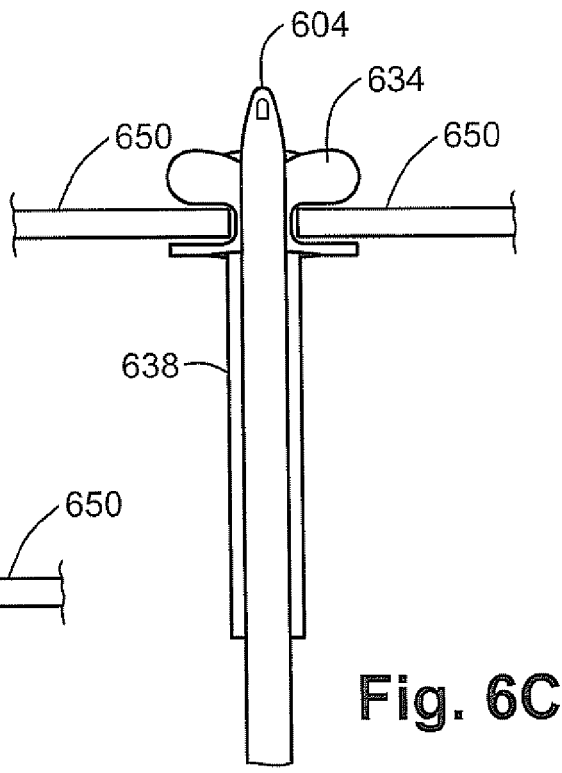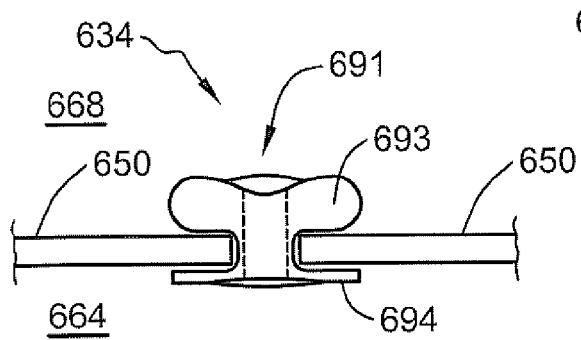
Fig. 6A
Fig. 6B
Fig. 6C
Fig. 6D

APPARATUS AND METHOD FOR IMAGING TISSUE

BACKGROUND OF THE INVENTION

1. Field of the Invention

The present invention relates to an apparatus and method for improving the imaging of tissue using a catheter for accessing, imaging and manipulating a body cavity in general, and to a catheter that has an imaging unit which emits and receives electromagnetic radiation or acoustic energy, and where such electromagnetic radiation or acoustic energy is utilized for imaging, locating and manipulating biological tissue.

2. Discussion of the Related Art

In 1806 Bozzini introduced the first instrument for electromagnetic radiation assisted visualization of a bodily cavity. He devised the first Cystoscope. For approximately 200 years, the principle remained the same; a catheter with light source at one end and a set of lenses to transfer the images to the operator. Almost a hundred years later, in the late 1800's, the discovery of X-rays by Reontgen and Tesla led to the development of a new field in medicine called radiology. The discovery of X-rays has led to development of various imaging devices operational at a distance from the body. These devices include X-ray, Fluoroscopy, CT and the like. Marie curie's discovery of radiation emitting elements in the late 1800's together with the invention of Anger's gamma camera, some 60 years later, have led to the development of nuclear medicine. Nuclear medicine is used for therapy as well as imaging. Imaging is performed by detecting traces of radioactive emission and scattering. Nuclear medicine was used in medicine primarily to determine function rather than anatomy of an organ.

During the late 20$^{th}$ century the use of imaging catheters using visible light source and cameras invaded almost any body cavity or organ. These included the bowls, gynecological, respiratory, CNS and others. Blood vessels were not candidates for visible light and camera catheters due to their thickness, which is around 10 mm's. Blood vessels were imaged using a process called angiography. In Angiography, a catheter is introduced into a blood vessel and is advanced until the relevant area is reached. At this point Contrast material (substance with heavy Z element) is injected into vessel lumen while X-ray imaging is performed to image the outer contour of the vessel. Several drawbacks of the technique include; the use of nephrotoxic elements, poor imaging quality, limitations in three dimensional imaging due to observer view perspective. There is therefore a need in the art for intravascular imaging tool and technique that will reduce the need for heavy Z contrast material and that will increase sensitivity of imaging resolution. There is also the need for intravascular imaging that will allow a vascular surgeon to image the blood vessel wall with greater accuracy.

Other intra-cavity scopes using visible light source also have several disadvantages; they require a clean organ cavity and clear view to a target. The use of the recently developed autonomous intra-cavity imaging camera did not answer these issues. Some of these issues were answered by the use of sound wave technology to view intra-body and intra-vascular spaces. The use of Ultrasound (US), however, is limited as well since sound requires a fluid medium to be transmitted. Thus, ultrasound imaging is not available in air containing intra-body cavities such as the respiratory system and parts of the gastrointestinal tract. In addition, in the same manner as with light, sound is deflected by debris and inflammatory tissue. This may reduce imaging quality and depth in various inflamed tissues.

Today, imaging of the body can be realized in various formats from many different positions, using an array of instruments. However, some locations and situations still constitute a challenge. These include, inflamed, debris filled spaces. For example, unclean or inflamed Colon, chronically inflamed facial sinuses, inflamed middle ear and others. The unparallel move towards minimal invasive surgery demand from the surgeon to perform tissue manipulations in small dark and often debris filled spaces were imaging often becomes difficult. External imaging frequently fail to illustrate the three dimensional environment where a surgeon will work during an operation. In location where conventional imaging using visible light source and camera as well as US technology are ineffective, a need for an imaging device that will help the physician to perform tissue manipulation exists.

There is therefore a need in the art for an apparatus and method which allow better and enhanced imaging of internal parts of the body organs, cavity or tissue. This imaging apparatus should allow the operator to visualization anatomical and histological structures at locations where visible light imaging is imperfect, inadequate or impossible. There is also the need in the art for an in-organ or body cavity imaging system which allow for imaging of tissue beyond the range of visible light imaging. There is also a need in the art for imaging inside a body organ or cavity where imaging quality is unaffected by inflammatory tissue elements or foreign debris. Such a method will allow an operator to receive important information beyond what can be seen with the available visible light imaging devices and methods used today.

SUMMARY OF THE PRESENT INVENTION

It is an object of the present invention to provide a novel an apparatus and method for improving the imaging of tissue using a catheter, which overcomes the disadvantages of the prior art.

In accordance with the subject matter, there is thus provided a device for imaging body tissue, the device comprising a catheter for accessing body cavities the catheter having there within an ionizing radiation source for emitting ionizing radiation; and one or more ionizing radiation detectors for detecting ionizing radiation; and wherein the ionizing radiation source is located in proximity to the one or more ionizing radiation detectors; and wherein preferably a signal is emitted by the ionizing radiation source, said signal comprising photons or electrons, said photons or electrons are backscattered from the body tissue or provoke the body tissue to generate photons or electrons; and wherein said backscattering from the body tissue generated photons or electrons are detected by the ionizing radiation detectors.

In some embodiments of the subject matter, the device is further comprising one or more collimators located partially surrounding the ionizing radiation source for limiting the ionizing radiation emission.

In some other embodiments of the subject matter the collimators having there within one or more shaped tunnels allowing for the dispersion of photons or electrons.

In some other embodiments of the subject matter, the device further comprising an amplifier for amplifying the reflected or body tissue generated photons or electrons.

In some other embodiments of the subject matter the device is further comprising a stent.

In some other embodiments of the subject matter, the device is further comprising a stent holder.

In some other embodiments of the subject matter, the ionizing radiation detectors are made of any one of the following materials: Cadmium-Tellurium, Cadmium-Zinc-Tellurium, Silicone, Silicone-Carbide, or like materials.

In some embodiments of the subject matter, the ionizing radiation detectors comprise one or more scintillation optical fibers.

In some other embodiments of the subject matter, the device is further comprising a photomultiplier or a photodiode for amplifying the photons reflected or body tissue generated photons detected by the ionizing radiation detectors.

In some embodiments of the subject matter, the device is further comprising a shell, a motor and a cable, the cable is connected to the shell, the cable is rotated by the motor, said rotation is transferred to the shell.

In some other embodiments of the subject matter, the ionizing radiation source is para-centrally located and the collimator is peripherally oriented, whereby the rotation of the shell results in an extended scanning area.

In accordance with the subject matter, there is provided a device for imaging body tissue, the device comprising a catheter for accessing body cavities, the catheter having there within an ultrasound transducer for emitting sound wave energy; and an ultrasound wave detector for detecting ultrasound wave energy; and wherein the ultrasound transducer is located in proximity to the ultrasound wave detector; and wherein preferably a signal is emitted by the ultrasound transducer, said signal comprising ultrasound waves, said ultrasound waves are reflected from the body tissue; and wherein said reflected ultrasound waves from the body tissue are detected by the ultrasound wave detector.

In accordance with the subject matter, there is also provided a method of imaging body tissue, the method comprising the steps of emitting ionizing radiation from an ionizing radiation source, the ionizing radiation source is located within an catheter; and detecting backscatter radiation from the body tissue resulting from the emission of ionizing radiation from the ionizing radiation source within the catheter.

In some embodiments of the subject matter, the method is further comprising a step of identifying aperture location.

In some other embodiments of the subject matter, the method is further comprising the step of guiding catheter end through aperture.

In some other embodiments of the subject matter, the method is further comprising the step of pushing a stent partially through the aperture, using a stent holder.

In some other embodiments of the subject matter, the method is further comprising the step of removing the catheter and the stent holder.

BRIEF DESCRIPTION OF THE DRAWINGS

The present invention will be understood and appreciated more fully from the following detailed description taken in conjunction with the drawings in which:

FIGS. 2A and 2B, present a schematic graphic illustration of the spectral results of two Monte Carlo simulations of the operation of the apparatus, in accordance with a preferred embodiment of the subject matter.

FIG. 3A shows a schematic, partially detailed, lateral view of the human head with some details used for demonstrating the possible location of use of the apparatus, in accordance with a preferred embodiment of the subject matter FIGS. 3B and 3C schematically illustrate another embodiment of the apparatus, in accordance with a preferred embodiment of the subject matter.

FIG. 6A through 6D is a schematic illustration of a method for inserting a stent through bone orifice using the apparatus, in accordance with a preferred embodiment of the subject matter.

DETAILED DESCRIPTION OF THE PREFERRED EMBODIMENT

The present invention involves bodily intra-organ as well as intra-cavity and intra-tissue imaging (all referred to herein as intra-organ). The use of the term "intra-organ" refers to freely, to any imaging obtained from within a body whether inside a cavity, an organ, virtual space or a tissue. Using non visible light sources such as electromagnetic radiation or sound waves, the present invention overcomes disadvantages found in prior art inventions. The present invention uses application and detection of ionizing radiation employed to tissue in order to convert these signals into an image. This image is used by an operator to explore surrounding tissue, examine layers of tissue, and manipulate instrumentation in and around said tissue and the like. The present invention employs certain physical science principles such as Compton backscattering principle, Electron Backscattering principle, X-ray fluorescence as well as ultrasound reflection. The present invention is operative in imaging tissue and space where prior art devices are at a disadvantage. The present invention uses novel intra-organ catheter or probe having within its fabric a radiation emitting or sound sources, detecting systems and information storing or transmitting systems. After insertion of the catheter to an intra-organ space, such as a sinus, blood vessel, ear channel, bowl lumen and the like, said sources emit radiation or sound toward the tissue around them. Said radiation passes through surrounding tissue or is absorbed. Some of the radiation backscatter or sound waves are reflected back. Backscattered radiation or reflected sound is absorbed by specialized detectors located within the fabric of said catheter. Detected radiation and sound is then stored, transferred, deciphered and further manipulated to construct an image of the environment surrounding said catheter. The advantage of using ionizing radiation or ultrasound for imaging in locales where visible light is at a disadvantage is obvious to the person skilled in the art.

Figure 1A:
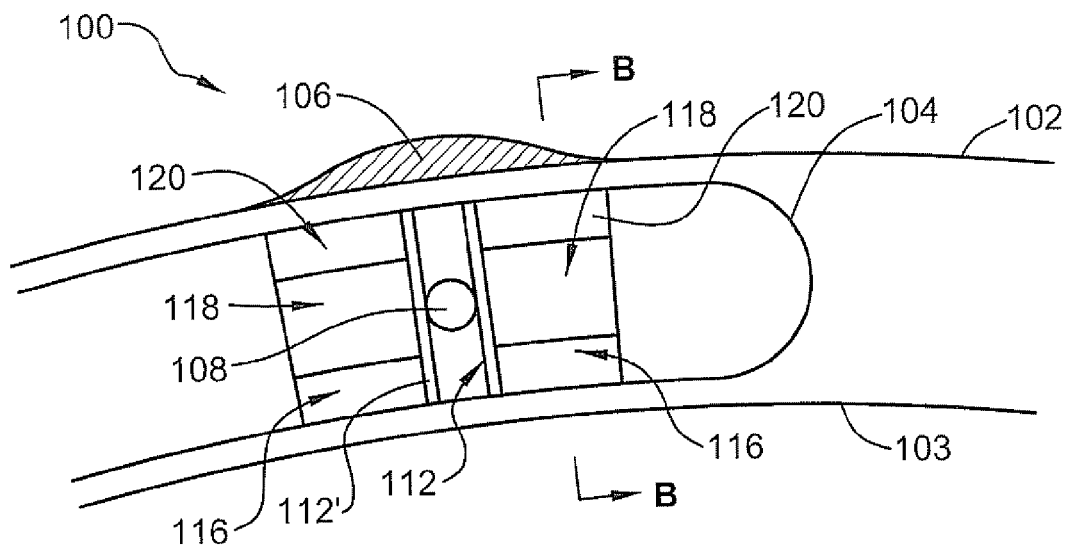
FIGS. 1A and 1B depict schematic illustration of the first embodiment of the apparatus, in accordance with a preferred embodiment of the subject matter.
Figure 1B:
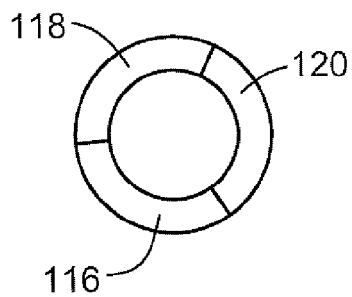
Figure 1C:
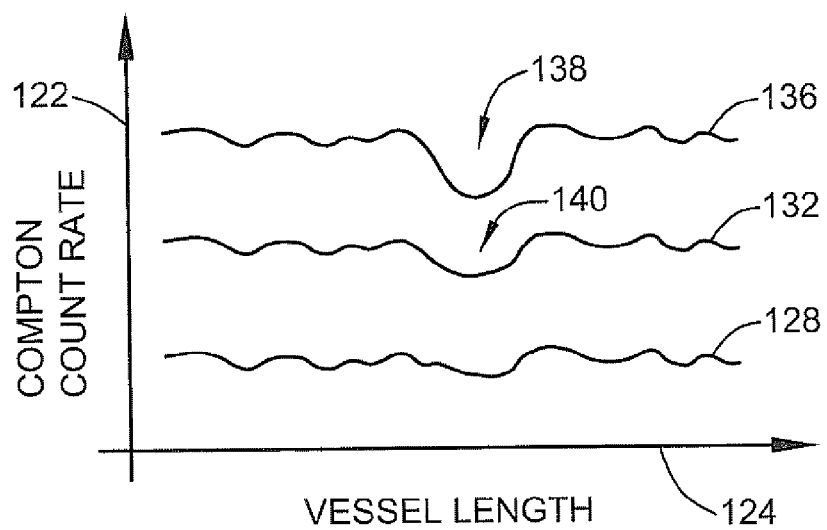
FIG. 1C shows a schematic graphic representation of the imaging principles of the embodiment presented in FIGS. 1A, 1B, in accordance with a preferred embodiment of the subject matter.

Reference is now made to FIGS. 1A through 1C, which are a schematic representation of the first embodiment of the apparatus of the present subject matter as well as a graphic presentation of data elucidated from the operation of the apparatus of the subject matter.

Referring now to FIG. 1A where the description of the first embodiment of the apparatus of the subject matter, generally referenced 100 invention and its usage in identifying blood vessel atheroma and Plaques is described. An atheroma is a deposit or degenerative accumulation of lipid-containing plaques on the innermost layer of the wall of an artery, where a plaque is a deposit of fatty material rich in calcium on the inner lining of an arterial wall, characteristic of atherosclerosis. Intravascular catheter generally referenced 100 is seen in a schematic cross-section inside blood-vessel walls 102 and 103 which are also depicted schematically in cross-section view. The blood vessel walls 102 and 103 have in the present example an atheroma 106 preferably within blood vessel wall 102. The intravascular catheter 100 is seen to be located within the boundaries of blood-vessel walls 102 and 103 where part of catheter body 104 is located in close proximity to atheroma 106. Within body 104 of catheter 100 and preferably close to catheter end is an energy emitting source 108. Such source may include any energy radiating source emitting, beta, x-ray or gamma particles. Source 100 may be for example Iodine$^{125}$ from MDS Nordion. Other forms of radiating sources may be used. These include Barium$^{133}$, Iodine$^{131}$, Phosphore$^{32}$, palladium$^{103}$ and the like. Around source 100, two collimators 112, 112' are shown in cross section. Collimators 112, 112' are in reality a three dimensional form of tube or a cone which limit the direction and spread of radiation cone. Collimators 112, 112' are typically made of high Z material such as Tungsten and the like, attached and surrounding collimators 112, 112' are detectors 116, 118 and 120. Detectors 116, 118, 120 are specialized detectors for radiation particles. Such detectors are made of material such as Cadmium-Tellurium, Cadmium-Zinc-Tellurium, Silicone, Silicone-Carbide and the like. A typical detector used in the present invention is Cadmium-Tellurium detector from Acorad Japan. Said detectors 116, 118, 120 are situated in a circular fashion inside body 104 of catheter 100. This can easily be perceived when examining a cross section of catheter 100 at line B of FIG. 1A. in FIG. 1B the three detectors 116, 118, 120 are seen to be arranged in a continuous circle and adjoining each other at their ends. Such arrangement serves to increase resolution of imaging. Single, multiple, longitudinal, circular, serial and any other configuration of detectors 116, 118, 120 which optimize detection resolution is possible. Detectors 116, 118, 120 detect radiation particles returning from irradiated surrounding tissue according to Compton's backscattering principle. Said data obtained by detectors 116, 118, 120 is sent to user via transmission techniques known in the art (not shown). Turning now to FIG. 1C where a schematic graphic representation of data received from detectors 116, 118, 120 is shown.

In the graph of FIG. 1C the abscissas 124 represent the length of the blood vessel walls 102 and 103 along which catheter 100 is traveling. The ordinates 122 represent vessel wall 102 and 103 density calculated using particle counts detected by said detectors according to Compton's backscatter principle or using Electron backscattering principle. Three graphs 128, 132, 136 represent density of vessel wall 102 and 103 calculated according to particle count rate detected by detectors 116, 118,120 respectively. Said graphs 128, 132, 136 represent vessel walls 102,103 densities measured by each detector along the travel path of said catheter 100. At the location of atheroma 106, vessel wall 102 density is lower compared with other locations along said wall 102. This is due to high fat content of the atheroma 106 and consequently of the vessel wall 102 as a whole. When ionizing radiation is directed toward this part of the wall, less radiation is back-scattered to detectors 116, 118, 120. Graph 128 calculated from particle count detected by detector 116 mainly from vessel wall 103 is approximately the same along the wall 103 length. Graph 128 vessel wall density variability depends on multiple factors such as vessel lumen corpuscles (not shown), minor variations in vessel wall 103 tissue elements (not shown) along wall 103 and the like. Graph 128 is relatively constant, indicating roughly similar density along vessel wall 103. Graph 132 and 136 also depict detected backscattered radiation particles count rate received by detectors 118,120 respectively from walls 102, 103, in the same manner as for graph 128. A count rate dip 138 is depicted along wave form 136 in a section of the graph. This count rate dip 138 indicates an area along vessel wall 103 where less returning particles were detected by detector 120 as compared with other parts of same wall 102. This lower detection rate represents an area of low density in vessel wall 102 and corresponds to the location of atheroma 106. Graph 132 represent particles detected from both walls 102,103. Small graph count rate dip 140 represents less particles returning from wall 102 at location of atheroma 106 compensated by returning particles from opposite location at wall 103 where no abnormality is found. Thus, count rate dip 140 is smaller than dip 138. Using multiple detectors of radiation particles returning from walls 102, 103 according to Compton's backscatter principle or electron backscattering principle is operative in identifying densities along walls 102, 103. This corresponds to vessel wall atheroma 106 as well as other vessel wall abnormalities such as plaques, aneurysm and the like. It should also be noted that each graph depicted in graph of FIG. 1C represent the cumulative particles detected by each detector at any time point of measurement. It should also be clear to the person skilled in the art that said density data can be used to map a vessel wall of any artery, vain, cavity, space or tissue through which catheter 100 is passed. In an exemplary operation of the subject matter, Catheter 100 is inserted percutanously into a vessel lumen. Catheter 100 is driven along the vessel length while imaging of vessel wall and surrounding tissue densities is performed. Data obtained by said detectors can be stored or transmitted. As seen above and herein, data can be depicted in graphs. Data can also be converted to other graphical representations such as a three dimensional view of said vessels and the like.

Figure 2B:
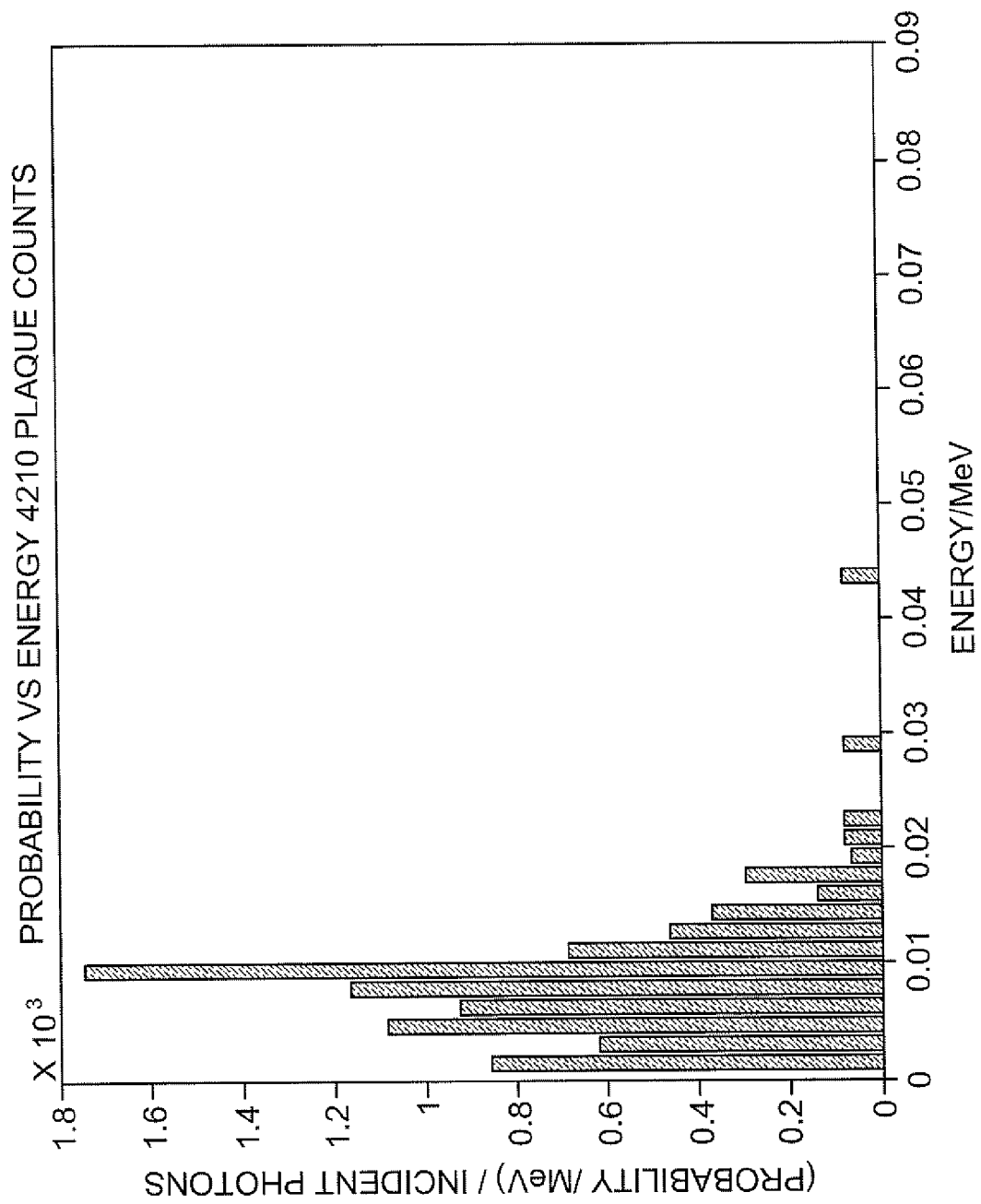

Reference is now made to FIGS. 2A and 2B, which is a schematic graphic illustration of the spectral results of two Monte Carlo simulations of the operation of the present subject matter. Both simulations represent the detection probability of backscattering beta electrons following irradiation of two different tissue samples by the imaging apparatus 100 of FIG. 1A of the present invention. The abscissas of FIGS. 2A, 2B represent the probability of detecting backscattered incident particles by the present subject matter. The Lower ordinate of FIGS. 2A, 2B represent total particle energy detected during the simulation. Upper ordinate of FIGS. 2A, 2B represent the probability of detecting electron backscattering particles of different energy from the two different tissue models. Tissue model represented in FIG. 2A is a blood vessel wall substantially having lipid rich area while tissue model represented in FIG. 2B is a blood vessel wall substantially excluding said lipid rich area. The density of blood vessel wall substantially excluding lipid rich area is close to 1 g/cm$^3$ where the density of blood vessel wall substantially having lipid rich area is lower, and is approximately 0.8 g/cm$^3$. When comparing results of the two simulations, it is clearly demonstrated that probability of detecting particle backscattering is higher in FIG. 2A then in FIG. 2B. The probability of returning backscattered particles detected by the present invention is increased by approximately 20% when simulating blood vessel wall substantially having lipid rich area as compared to lipid poor or substantially excluding lipid blood vessel wall. On top of upper ordinate of FIGS. 2A, 2B the probability of detecting backscatter particles or electrons of certain energy is calculated. In FIG. 2A, representing blood vessel substantially excluding lipid rich area, the calculated probability is 4623 counts per second. In FIG. 2B, representing blood vessel substantially having lipid rich area, the calculated probability is 4210 counts per second. The probability calculated is an indirect measure of blood vessel wall density and thereby blood vessel constitution. This Monte Carlo simulation provide conceptual proof to the ability of the subject matter to identify and separate different blood vessel wall constitutions and is functional in ascertaining the proper operation of the present apparatus and method of the subject matter.

FIGS. 3A, 3B, 3C are schematic representation of another embodiment of the apparatus of the subject matter. The present embodiment is operative in intra-organ imaging such as the nasal sinuses, external ear, nasal cavity, pharynx as well as other real and virtual spaces within the body where a catheter can be inserted to. The present invention embodiment shown in FIGS. 3A, 3B, 3C is exemplified by its use in the intra-organ imaging of the human facial sinuses and the placement of a stent in an aperture between two communicating sinuses (see also FIG. 6). In FIG. 3A a schematic lateral axial view of a human head 360 is shown where some partial in depth view of the nasal sinus 364, frontal sinus 368 frontonasal sinuses aperture 376 and nares 372 are shown. Catheter 300 of the present invention is shown inserted through nares 372 along the nasal cavity where catheter end 304 is shown in close proximity to aperture 376. An operator skilled in handling intra-organ catheters can easily insert and manipulate said catheter within the sinuses. In FIG. 3B catheter 300 is shown in greater details, where catheter body 304 is a part of catheter 300 and is used here to refer to the end part of catheter 300 where imaging unit 301 reside there within. Catheter 300 further comprises an amplifier 330, sinus stent 334 and stent holder 338 as well as cable 342, slip ring 346 and motor 350. In FIG. 3C part of area 305 of FIG. 3B is exploded where imaging unit 301 which reside inside catheter body 304 is visible. Imaging unit 301 seen in FIG. 3C is shown in exploded view to provide a clearer view of the inside of said imaging unit. Said imaging unit 301 comprises energy emitting source 308 surrounded by collimator 312. Said collimator 312 encapsulate source 308 incompletely such that ionizing radiation from source 308 can exit via a cone shape tube 313 like opening leading from source 308 to preferably outside of imaging unit 301. cone shape tube 313 surrounded by collimator 312 is designed such that the proximal part, closer to source 308, is smaller in diameter then the distal part, which is further from source 308. This configuration allow for a cone distribution of ionizing radiation emitting from source 308 through tube 313. Collimator 312 is typically made of high Z material such as Tungsten, Ceramics, High density plastics and the FIG. 3C, source 308 and collimator tunnel 313 are shown in mid position of imaging unit. In accordance with other exemplary embodiments of the present subject matter, any other spatial position of source 308 and collimator tube 313 can be used to obtain the desired effects of the present subject matter and such are contemplated within the present description. This may include an off-center location of source 308 as well as tube 313 spatial tilt, or any other variation. A preferable source and cone tube positioning of the present embodiment include an off center location of source 308 and a spatial cone tube 313 of one to sixty degrees. Any other configuration of source 308 location, size, material as well as collimator tube 313 length, diameters, tilt and attitude are possible in the context of the present invention. Source 308 is like source 108 of FIG. 1A and may include Barium$^{133}$, Iodine$^{131}$, Phosphore$^{32}$, palladium$^{103}$ and the like. Source 308, like source 108 of FIG. 1 emits ionizing radiation particles (not shown). Illustrated on top of collimator 312 and having tube 313 pass there within is detector 316, shown here as two semi circles. In FIG. 3C imaging unit 301 is halved and separated to provide a better understanding of inner parts and their relations. In reality detector 316 is a circular unit having an aperture there within which constitute one end of tube 313. Detector 316 may be located in any location along and around and within catheter 300 in order to increase the resolution of imaging. Multiple detectors may also be realized within the same catheter 300 to provide enhanced resolution of imaging. Detector 316 is operative in detecting backscattering ionizing radiation returning from tissue as is described for detectors 116,118, 120 of FIG. 1. Detector 316 can also be an X-ray Fluorescence Photons (XRF) detector such as Silicone-Carbide detector from Advanced Photonics inc. When detector 316 is an XRF detector, it is operative in detecting photons returning from elements excited by ionizing radiation first dispensed by source 308. Such elements may include calcium atoms in bone Source 308, collimator 312 and detector 316 along with resulting tube 313 are constructed together in a shell casing 309. Shell casing 309 is made of Tungsten and the likes, high Z material with high specific density. Referring now back to FIG. 3B where other parts and operations of the present invention are unfolded. Catheter 300 is depicted where a central axis line 352 is passing there within. Catheter imaging unit 301 encased in shell 309 is preferably located within catheter body 304. Imaging unit 301 is connected to cable 342. Cable 342 is a plastic or metal wire flexible material such as used in guide wires in cardiac catheters and the like, connected to slip ring 346 which is connected to motor 350. In another embodiment of this invention, the catheter is made from rigid material such as a metal or plastic tubing and the procedure is done in a strait line from the operator outside to the area of interest. Motor 350 is an electric motor, preferably brushless with an encoder to record angular position or a step motor to enable tracking angular position. Motor 350 is operative in providing rotational energy thorough cable 342 to imaging unit 301. Rotation of imaging unit 301 provide for further image resolution. Combining a para-axial placing of source 308 or of tube 313, or tilting of tube 313 and rotational movement of imaging unit 301 provide for a non central cone emission of ionizing radiation. As imaging unit 301 rotate, source 308 emit ionizing radiation particles to surrounding tissues. Backscattering radiation is detected over time upon detector 316. Data is registered from detector 316 over time. The data may include particle flux, incident angle of detection, imaging unit 301 rotational speed and location as well as other parameters. Said data is used to compute and illustrate an image of surrounding tissue similar in fashion to description provided in FIG. 1C. In one possible imaging configuration, the operator is shown an image of brightness as a function of angle. The operator's objective then, is to find a dark spot target representing less backscattering or no XRF in the case of x-ray fluorescence imaging. When operator identified target, he guide the catheter so that the dark spot target is in the center of the imaging screen. This image scene is translated in reality to the catheter being located proximally in front of the target. Other Imaging configurations are within the subject matter, such as a geographical image, a two dimensional or three dimensional images and the like Data detected by detector 316 is transferred via cable 342 and slip ring 346 to a remote location where data is analyzed and displayed (not shown). In another embodiment of this invention, the output of the catheter can be sound wave energy that is proportional to the rate of photons or electrons that are detected. The operator (not shown) find the area where there is minimal count rate during a scan signifying the detection of a hole in the bone. It should be clear to the person skilled in the art, that other possibility of the subject matter include said catheter 300 without motor 350, where catheter 300 is manually manipulated. Manual manipulation of catheter 300 can be performed by an operator and used in the same manner as explained above and herein. Follows is an example of operation of catheter 300 using XRF detection for opening an edematous an inflamed frontal sinus 378. Operator (not shown) insert catheter 300 into nasal cavity 364 through nares 372. Operator direct catheter body 304 towards aperture 376. Scanning of the target area via catheter 300 is started. Ionizing radiation is emitted in a circular fashion from source 308 via tube 313. Ionizing particles impact on calcium atoms in the bony structure of the nasal cavity causing emission of XRF photons. Said photons are detected by detector 316. Data detected by detector 316 is then transferred via cable 342 and slip ring 346 to a remote location where computations are performed to provide the operator with a visual image of the boney structures around body 304 part of catheter 300. The visualization of aperture 376 between frontal sinus 368 and nasal space 364 is then easily realized even in the presence of inflamed and edematous tissue surrounding said aperture. Operator, then direct body 304 of catheter 300 towards aperture 376 and passes part of body 304 of catheter 300 through aperture 376. Stent holder 338, a tubular body wrapped around catheter 300 operational in holding and advancing stent 334, also wrapped around catheter body 304. Stent 334 is described in detail in FIG. 6, and is operative in draining sinus 368 and cavity 364 connected by aperture.

At this time, operator slide stent holder 338 and stent 334 towards end of body 304 until stent 334 partially passes aperture 376 in such a manner to be positioned firmly between frontal sinus 368 and nasal cavity 364 and through aperture 376. At this time, operator withdraws catheter 300 and stent holder 338 from human 360, leaving stent 334 draining frontal sinus 368.

Figure 4:
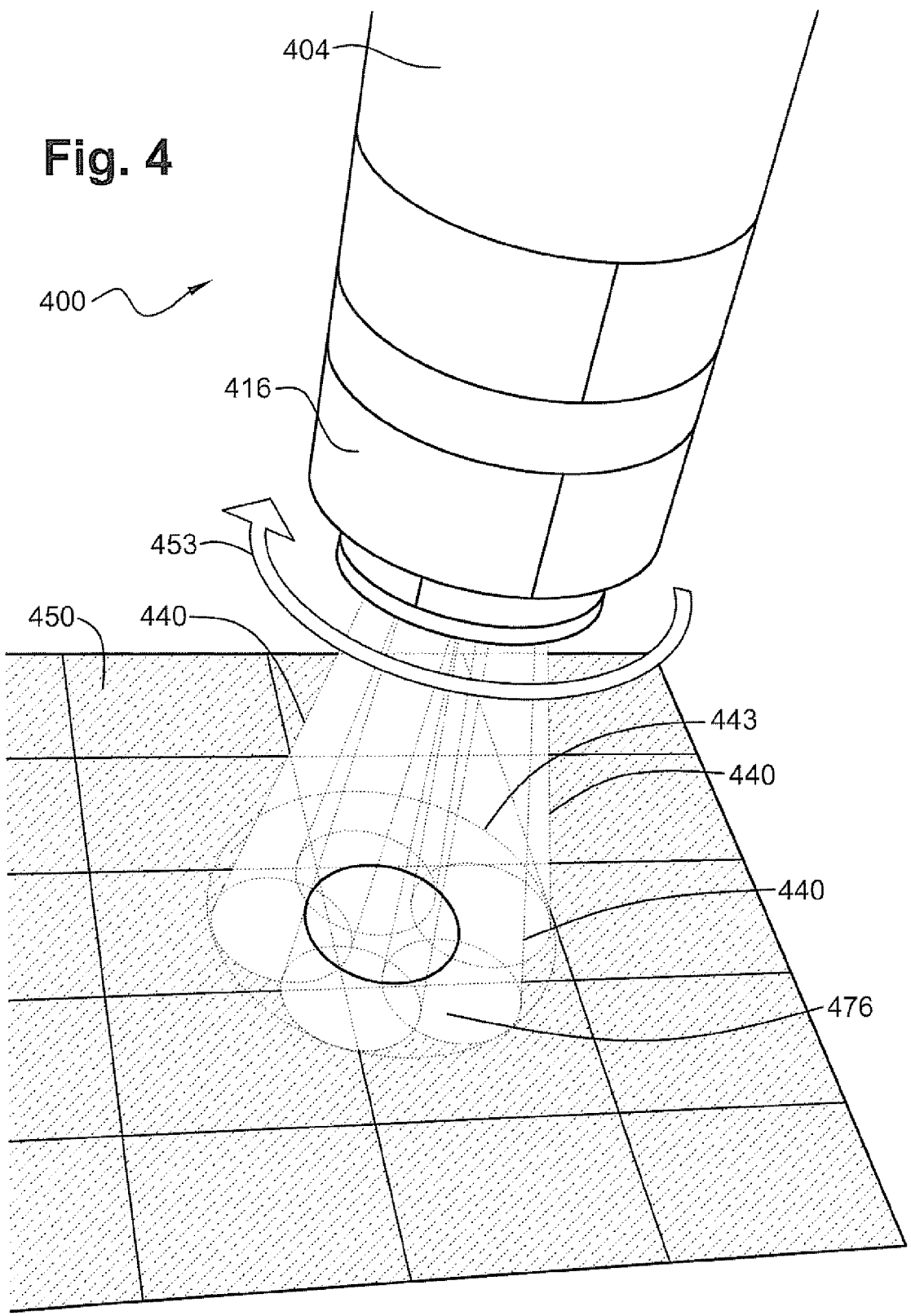
FIG. 4 shows a schematic three dimensional view illustrating an imaging unit scanning operation, in accordance with a preferred embodiment of the subject matter.

FIG. 4 is a three dimensional illustration of the utilization of para-central or tilted radiation cone in detecting an aperture in a bony structure through the use of XRF signal. Surface 450 is a schematic depiction of a bony structure having Calcium ions within its fabric. Surface 450 is a continuous surface interrupted by aperture 476. Aperture 476 represents an opening or a defect in surface 450 fabric. Catheter 400 body 404 is situated in close proximity to aperture 476 where imaging unit 401 is directed approximately towards aperture 476. Arrow 453 indicates rotation direction of imaging unit 401. It should be appreciated that opposite direction rotation as well as other tilting motions of imaging unit 401 is within the scope of the present subject matter. Several radiation cones 440 are shown together emanating from imaging unit 401 and ending on surface 450 and aperture 476. It should be understood that due to limitations of the illustration to simulate three dimensional real live actions, arrow 453 infers rotational movement to imaging head 401. Similarly, the several cones 440 represent one radiation cone 440 at several intervals in time during said rotation in operation ionizing radiation cone 440 is emanating from imaging unit 401 and is a schematic realization of ionizing radiation particles spreading in a cone like fashion towards surface 450. Due to rotation of imaging unit 401 the radiation cone can scan a large surface area in time as exemplified by line 443. In an exemplary situation where catheter 400 is used to image and locate aperture 376 of FIG. 3 dividing sinus 368 and cavity 364 of FIG. 3 is typically 5 mm by 5 mm. An operator skilled in the art can easily guide catheter 400 to said location. Said rotation also results in overlapping of surface scanning by said cones 440. Using overlapping cones facilitate scanning of surface 450 and provide returning XRF particles from different locations and angles, thus increasing speed and accuracy of imaging. This operating model described here and above, is used to locate bony structures located under edematous soft tissue or bony structure obscured by debris and inflammation etc. An operator (not shown) can easily thus locate a specific location in a bony structure, such as an aperture, hidden under obscuring soft tissue layer. The operator can also manipulate said catheter 400 through the soft tissue and access a specific location on the bony structure at hand. Catheter 400 can also be utilized to image other bony structures such as those of the nasal cavity, sinus walls, middle ear bones and others. Other radiation sources can also be realized such as Gamma particles and the like where soft tissue structures can also be realized. In such a model a visual light and camera may also be combined with catheter 400 such that their use can be interchanged according to need. This visual and non visual combination can reduce the amount of radiation needed for a specific imaging task. Combination of backscattering imaging as described in FIG. 1 and X-ray fluorescence imaging described here and above and in FIG. 3 can also be combined in one device. In such a device (not shown) two different detectors can be combined in many different positions, such that photons of XRF, typically in the range of 4 Kilo electron volt (Kev), are detected in one detector and particles backscattered, typically in the range of 25-30 Key, are detected in a second detector. This combination increases imaging capabilities of the present invention owing to long distance detection realized by Compton backscatter and short distance detection realized by XRF. Further combination of XRF and Compton backscatter imaging with a visual light and camera imaging system also is within the scope of the present invention to provide multiple imaging capabilities in one device. Other combinations of imaging head attitudes are also realized in the scope of the subject matter. These can include an imaging unit 416 having scanning cones directed from the side of the catheter 400 in different angles and directions. This configuration allow for scanning and imaging of tissue all around catheter body 404 Within the subject matter include a combination of ultrasound system to work concurrently with the subject matter such that a dual system of ultrasound and the subject matter can be located and operated from the same catheter or from two different catheters.

Figure 5B:
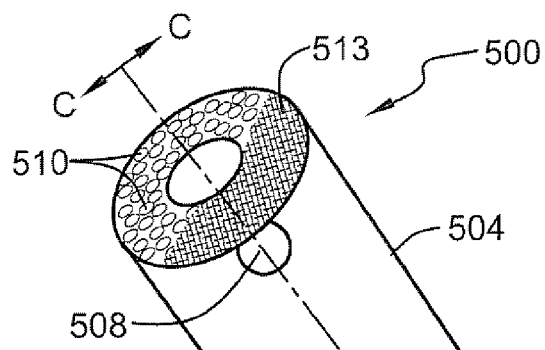
FIG. 5A through 5C are schematic illustrations of yet another embodiment of the apparatus utilizing scintillation fiber optics, in accordance with a preferred embodiment of the subject matter.
Figure 5C:
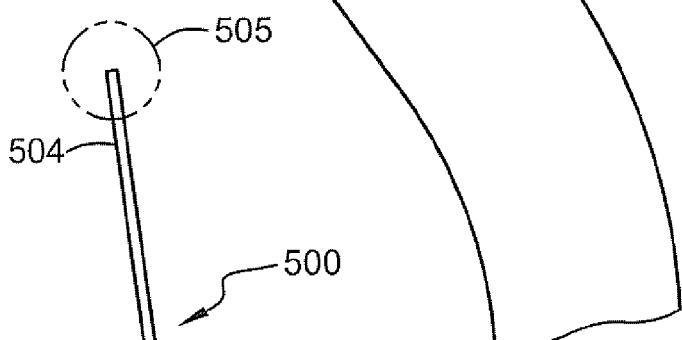
Figure 5C:
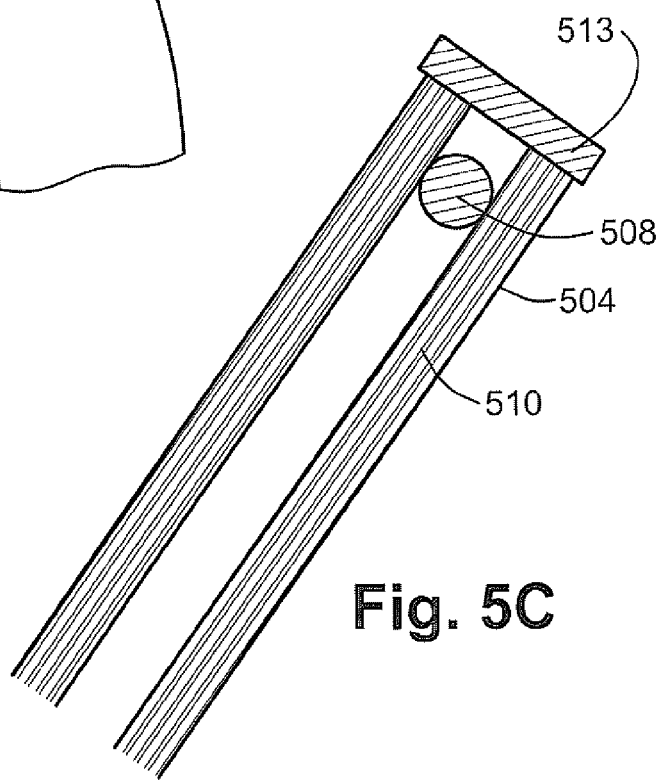
Figure 5A:
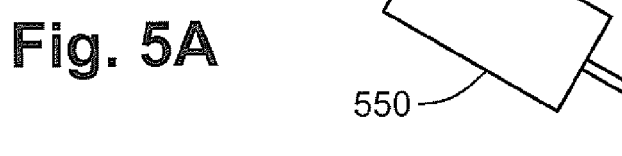

Turning now to FIGS. 5A, 5B, 5C where an imaging system using optical fiber and scintillation paint is used to detect Compton backscatter. FIG. 1A is a schematic presentation of the system, FIG. 1B is an explosion of area 505 of FIG. 1A, and where FIG. 1C is a cross section at lines C of FIG. 1B. An alternative embodiment of the present invention is presented where catheter 500 is composed of catheter body 504 having within and close to catheter 500 end radiation source 508 covered partially by collimators (not shown) and surrounded by one or a multitude of optical fibers 510. Said optical fibers are covered at their sensing end by scintillation paint 513 or like material. In FIG., 5, scintillation paint 513 and optical fibers 510 ends are shown together. In reality, optical fibers 510 ends are covered with scintillation paint 513 such that catheter 500 end is covered by scintillation paint 513 and optical fibers 510 are invisible to the naked eye. Optical fibers 510 covered by scintillation paint 513 are known in the art. Such optical fibers can be a BCF-12 scintillation optical fibers from Saint-Gobain crystals and the like. Radiation source 508 is similar to radiation source 108 of FIG. 1 and source 308 of FIG. 3. As in previous discussion, source 508 is partially covered by collimators (not shown) such that ionizing radiation is directed to specific predetermined areas out side of catheter 500. This creates radiation cones (not shown) similar to radiation cones 440 of FIG. 4. In FIG. 5B, optical fibers 510 are circularly arranged around source 508 such that radiation emanating from source 508 is understood to be radiating through center of catheter 500, It should be understood that the depiction in FIG. 5 is merely an illustration, where in reality, radiation cone can be arranged to emanate to all direction around said source. In operation, catheter 500 is inserted into a body cavity, organ or tissue, as seen for example in FIG. 3A. Source 508 emits beta particles in a similar fashion to source 308 and 108 of FIGS. 3 and 1. Backscattering particles are absorbed by scintillation optical fibers. This data is conveyed to photomultiplier 550 or photodiode. Photomultiplier 550 is operative in enhancing photons detected by optical fibers 510 and is connected to said fibers at a downstream location. Photomultiplier 550 can be a photomultiplier tube R9779 from Hamamatsu corp and the like. Signals enhanced by photomultiplier 500 are conveyed or transmitted to a remote location. In the context of this invention, Catheter 500 can also be realized as made of a mixture of visual light detecting optical fibers along with scintillation detecting optical fibers such that both radiation particles and photons can be detected thus enhancing the possibilities of the present invention. Using multitude of optical fibers in a bundle form increases the imaging resolution of the present invention and is also realized here.

In FIGS. 6A, 6B, 6C, 6D another embodiment of the present subject matter and a method for inserting an interosseous stent are schematically illustrated. In FIG. 6A catheter 600 is situated spatially in close proximity to bone plates 650 while catheterend604 is directed toward aperture 676. Catheter 600 comprises catheter body 642 and catheter end 604. Within catheter body 642, close to catheter end 604 is an imaging unit 601. Imaging unit 601 can be the same as imaging units 101 or 301 of FIGS. 1, 3. An alternative imaging unit 601 of the present subject matter, further described herein, is an ultrasound imaging unit comprising an ultrasound transducer (not shown) such as Acuson Antares EC9-4 Endocavity Probe from Siemens. Other miniature piezoelectric transducers working in the range of 3-200 MHz can also apply. Imaging unit 601 further comprises Ultrasound detector (not shown) such as a miniature piezoelectric transducers and information transmission means (not shown) such as an CC 1110 RF transceiver chip from Texas Instruments. Installed on catheter 600 is stent 634 and stent holder 638. Stent 634 is preferably constructed from a polymer material. Other materials can also be realized such as Nitinol metal which has a memory for a certain shape "programmed" to it, and the like. Stent 634 is designed for providing a stable patent connection between space 668, and space 664 connected normally by aperture 676 of FIG. 6A. Said aperture 676 may be occluded as was exemplified for aperture 376 of FIG. 3A. In such cases movement of material from space 668 to space 664 through aperture 676 is hindered or stopped in the same manner as was described for occlusion of aperture 376 between sinus 368 and nasal cavity 364 of FIG. 3A. In design, stent 668 is a tube like structure having an inner patent hollow 691 and preferably two or more outer circumferential projections 693 and 694. Both projection 693 and 694 are designed to be flexible such that they easily bend and twist with application of force Stent holder 638 is an apparatus of tubular form with a diameter preferably larger then catheter 600 but sufficiently small to allow some minor friction between catheter 600 and stent holder 638. Stent holder 638 is attached to stent 634 via stent holder 638 is sufficiently long to allow operator to manipulate stent 634 along catheter 600 from a location distant to catheter end 604. In operation, operator (not shown) manipulate catheter 600 to close proximity of aperture 676 location as seen in FIG. 6A. Ultrasound imaging unit 601 is used to guide operator toward aperture 676. Other imaging units 101 and 301 described earlier can also be used to locate said aperture. When aperture 676 is located, operator advance catheter end 604 through aperture 676 as seen in FIG. 6B. Operator then uses stent holder 638 to push stent 634 partially through aperture 676 as seen in FIG. 6C. Catheter 600 and stent holder 638 are then removed. As seen in FIG. 6D stent 634 is left spanning between plates 650, preferably obliterating natural aperture 676. Stent hollow 691 is now bridging between space 668 and space 664, permitting the passage of material from one space to the other. Thus in operation, said catheter system can be used to locate, enter and bridge hidden and obstructed bony orifices.

It will be appreciated by persons skilled in the art that the present invention is not limited to what has been particularly shown and described hereinabove. Rather the scope of the present invention is defined only by the claims which follow.

We claim:

1. A device for imaging body tissue, the device comprising:
a catheter for accessing body cavities, comprising:
a radiation source (108) for emitting beta radiation, and
at least one detector (116, 118, 120) for detecting the beta radiation, and
wherein said at least one radiation source (108) is located in proximity to said at least one detector (116, 118, 120), and
wherein said at least one detector is configured for detecting electrons backscattered from the body tissue in response to said radiation source.

2. The device of claim 1 further comprising at least one collimator located partially surrounding said at least one radiation source for limiting the radiation emission.

3. The device of claim 2 wherein said at least one collimator having there within an at least one shaped tunnel allowing for the dispersion of electrons.

4. The device of claim 1 further comprising an amplifier for amplifying the backscattered electrons.

5. The device of claim 1 further comprising a stent.

6. The device of claim 1 further comprising a stent holder.

7. The device of claim 1 wherein said at least one detector comprises a material selected from the group consisting of Cadmium-Tellurium, Cadmium-Zinc-Tellurium, Silicone, and Silicone-Carbide.

8. The device of claim 1 wherein said at least one detector comprises at least one scintillation optical fiber.

9. The device of claim 8 further comprising a photomultiplier or a photodiode.

10. The device of claim 1 further comprising a shell, a motor and a cable, the cable is connected to the shell, the cable is rotated by the motor, said rotation is transferred to the shell.

11. The device of claim 10 wherein the radiation source is substantially centrally located and the at least one collimator is peripherally oriented, whereby the rotation of the shell results in an extended scanning area.

12. The device of claim 11 further comprising a second radiation source for emitting X-ray or gamma radiation and a detector configured for detecting X-ray fluorescence (XRF) photons provoked by the body tissue in response to emission of said X-ray or gamma radiation.

13. A method of imaging body tissue, the method comprising the steps of;
emitting electrons from a beta radiation source, said beta radiation source is located within a catheter, and
detecting electron backscattering from the body tissue resulting from the emission of beta radiation from said beta radiation source within said catheter.

14. The method according to claim 13, further comprising a step of identifying aperture location.

15. The method of claim 13 further comprising the step of guiding catheter end through aperture.

16. The method of claim 13 further comprising the step pushing a stent partially through the aperture, using a stent holder.

17. The method of claim 13 further comprising the step of removing the catheter and the stent holder.

* * * * *